US008652033B2

(12) United States Patent
Berci et al.

(10) Patent No.: US 8,652,033 B2
(45) Date of Patent: Feb. 18, 2014

(54) VIDEO STYLET WITH DIRECTABLE TIP

(75) Inventors: George Berci, Los Angeles, CA (US); James P. Barry, Charlton, MA (US)

(73) Assignee: Karl Storz Endovision, Inc., Charlton, MA (US)

( * ) Notice: Subject to any disclaimer, the term of this patent is extended or adjusted under 35 U.S.C. 154(b) by 94 days.

(21) Appl. No.: 12/889,095

(22) Filed: Sep. 23, 2010

(65) Prior Publication Data
US 2012/0078055 A1 Mar. 29, 2012

(51) Int. Cl.
*A61B 1/267* (2006.01)

(52) U.S. Cl.
USPC ........................................... 600/199; 600/185

(58) Field of Classification Search
USPC ............. 600/120, 185–200, 112; 128/200.26; 348/77
See application file for complete search history.

(56) References Cited

U.S. PATENT DOCUMENTS

| | | | |
|---|---|---|---|
| 4,742,819 A | 5/1988 | George | |
| 5,313,306 A * | 5/1994 | Kuban et al. | 348/65 |
| 5,363,838 A | 11/1994 | George | |
| 5,375,401 A * | 12/1994 | Flickinger | 56/239 |
| 5,800,344 A * | 9/1998 | Wood et al. | 600/188 |
| 5,856,819 A * | 1/1999 | Vossler | 345/102 |
| 6,313,868 B1 * | 11/2001 | D'Alfonso et al. | 348/72 |
| 6,322,498 B1 | 11/2001 | Gravenstein et al. | |
| 6,929,600 B2 | 8/2005 | Hill | |
| 7,297,105 B2 | 11/2007 | Mackin | |
| 7,543,327 B1 * | 6/2009 | Kaplinsky | 725/105 |
| 7,658,708 B2 | 2/2010 | Schwartz et al. | |
| 7,995,096 B1 * | 8/2011 | Cressy et al. | 348/153 |
| 2001/0048983 A1 * | 12/2001 | Yoshida et al. | 428/34.1 |
| 2004/0215061 A1 | 10/2004 | Kimmel et al. | |
| 2005/0266798 A1 * | 12/2005 | Moloney et al. | 455/41.2 |
| 2007/0049794 A1 | 3/2007 | Glassenberg et al. | |
| 2007/0129603 A1 | 6/2007 | Hirsh | |
| 2007/0270642 A1 * | 11/2007 | Bayer et al. | 600/109 |
| 2008/0177146 A1 | 7/2008 | Chen | |
| 2008/0236575 A1 | 10/2008 | Chuda | |
| 2009/0182342 A1 * | 7/2009 | Bhatnagar et al. | 606/99 |
| 2009/0187072 A1 * | 7/2009 | Manohara et al. | 600/109 |
| 2009/0322867 A1 | 12/2009 | Carrey et al. | |
| 2010/0094090 A1 | 4/2010 | Mejia | |
| 2010/0179384 A1 | 7/2010 | Hoeg et al. | |
| 2010/0224187 A1 | 9/2010 | Dalton | |
| 2011/0078625 A1 * | 3/2011 | Mumford et al. | 715/804 |
| 2011/0137127 A1 * | 6/2011 | Schwartz et al. | 600/188 |
| 2012/0022326 A1 * | 1/2012 | Jaime | 600/109 |
| 2012/0035502 A1 * | 2/2012 | Menegazzi | 600/567 |

FOREIGN PATENT DOCUMENTS

| | | |
|---|---|---|
| WO | 2008019367 A2 | 2/2008 |
| WO | 2009051698 A2 | 4/2009 |

OTHER PUBLICATIONS

European Search Report; Application No. EP 11182551.9-2319; Issued: Jan. 19, 2012; Mailing Date: Jan. 30, 2012; 8 pages.

* cited by examiner

*Primary Examiner* — Jan Christopher Merene
(74) *Attorney, Agent, or Firm* — St. Onge Steward Johnston & Reens LLC (57) ABSTRACT

A video intubation system that provides for multiple image streams to be simultaneously presented to a user, the first image stream generated by a video laryngoscope and the second image stream generated by a video stylet. The video stylet is provided with a deflection section for ease of introducing an ETT into the trachea of a patient, the video stylet having a pistol-type grip and a control interface in the form of a trigger-type lever to facilitate comfortable griping and manipulation by the user.

7 Claims, 8 Drawing Sheets

VIDEO STYLET WITH DIRECTABLE TIP

FIELD OF THE INVENTION

The invention relates to a video stylet with a tip that may be directed by a user, and more specifically, to a combination video stylet and the video laryngoscope combination where both the video stylet and laryngoscope are provided with a similar image sensor providing a split screen view for the user.

BACKGROUND OF THE INVENTION

During a medical procedure that requires the patient to be anesthetized, the patient's breathing functions are temporarily disabled. Ventilation is supplied to the patient through an endotracheal tube. This tube is inserted into the trachea, and is typically closed against the wall of the trachea by an inflatable cuff. However, the insertion of the tube involves risks, such as, damage to the vocal cords and a prolonged intubation procedure in which the patients breathing is stopped but oxygen is not yet delivered to the patient as the tube has not yet been inserted. It is estimated that about one third of deaths occurring during a surgical procedure while under anesthesia for morbidly obese patients are associated with the intubation process.

Some of the difficulties the user encounters include: the restriction of view as the tube is inserted, variations in the anatomy of the patients, an uncomfortable and unnatural position for the anesthesiologist while holding the instrument and the necessity for rapid intubation.

With the advent of video laryngoscopes and cameras, instrumentation has been improved to the extent that it can enable viewing of the cords and larynx on a video screen thereby facilitating the intubation of the patient in a relatively quick and safe manner. For example, U.S. Pat. Nos. 6,890,298, 6,875,169 and 7,044,909 are variously directed toward video imaging systems. However, typically the view provided by the equipment has been limited requiring more time for the user to intubate the patient.

For example, video laryngoscopes have been used to help facilitate the intubation of a patient. Video laryngoscopes typically contain a light guiding system, usually in the form of fiber optic cables, in order to bring light to the surgical area. Video laryngoscopes also typically contain an image guiding system, for example in the form of a rigid rod lens system, arranged in the blade of the laryngoscope, or in the form of an ordered, flexible fiber optic bundle. In these configurations, the image guiding system is utilized to transmit reflected light from the area ahead of the blade to a camera, which may be attached to the laryngoscope. Alternatively, it is known to affix an imager, which may comprise, for example, a Charge Couple Device (CCD), or Complementary Metal Oxide Semiconductor (CMOS) to the distal end of the laryngoscope blade. In this case, the image data may be transmitted to the camera affixed to the laryngoscope via electrical wires (or wirelessly) as digital image data.

While this configuration for a video laryngoscope does provide a user very useful information in the form of image data, a major problem with current systems is the limited field of view. For example, when the user is intubating the patient, the imaging device, typically positioned on the underside and distal end of the laryngoscope blade, only provides a view of the, roughly, two-thirds of the configuration of the anatomy (depending on the patient it could be more or less) with the lower one-third not visible to the user. This is because the laryngoscope is only advanced into the throat of the patient far enough to lift the tongue (the upper anatomy part of the epiglottis and the vocal cords) and facilitate the introduction of the Endotracheal Tube ("ETT", and which typically comprises a flexible plastic) into the trachea.

A malleable aluminum stylet is an accessory used with the ETT (typically inserted into the tube) to provide the tube with additional rigidity for the intubation process. The anatomy of patients often requires that the tip of the ETT to have a sharper bend and be partially more rigid so as to introduce it through the vocal cords, which are located toward an anterior (at the 12 o'clock) position. The stylet, which may comprise a malleable aluminum rod covered with a plastic material (disposable) is slid inside the ETT and is used to increase the bend of the tip of the ETT and form the proper angulation for the particular patient. After intubation, the stylet is removed and the ETT remains in place.

So, a major problem with current systems is two-fold, 1) if the stylet is not provided with the proper angulation or bend radius prior to insertion of the ETT, the user must remove the ETT and bend the stylet to match the patient's particular anatomy (which takes additional time and is highly undesirable); and 2) as the ETT (and stylet) is advanced through the vocal cords, the view in front of the ETT blocked by the stylet and ETT.

While current systems do provide a view from the bottom of the laryngoscope blade, this view is limited to the upper portion of the patient's anatomy.

SUMMARY OF THE INVENTION

It is therefore desired to provide an improved video laryngoscope system that provides the user with a greater field of view.

It is also desired to provide an improved video laryngoscope system that allows the user to see virtually all of the larynx and the trachea as the ETT is advanced.

It is further desired to provide an improved video laryngoscope system that facilitates a quicker intubation and reduces the probably of injuring the patient.

It is still further desired to provide an improved video laryngoscope system that is relatively comfortable for the user to grip.

It is also desired to provide an improved video laryngoscope system that provides enhanced control to the user for the intubation process.

These and other objectives are achieved by the provision of a video laryngoscope system that provides a split image simultaneously to a user, such that, the user is provided with a greater field of view.

Accordingly, in one advantageous embodiment, the video laryngoscope system includes a video laryngoscope having an imaging device positioned at a distal end of the blade and a flexible stylet having an imaging device positioned at a distal end of the stylet. The two imaging devices provide two different views of the patient's anatomy during the intubation process. These two image streams may then be presented to the user on a display(s) (e.g., two different monitors positioned side-by-side or a single monitor provided with a split screen). This provides the advantage that the user is presented with a view of the upper portion of the patient's anatomy via the laryngoscope as well as being presented with a view in front of the video stylet as the stylet is advanced through the trachea.

It is contemplated that the video stylet may be provided as a flexible member that allows the user to actuate the tip allowing the tip to deflect to the proper angulation or bend radius for the patient's particular anatomy. This provides the further benefit that the video stylet does not need to be removed from the trachea in order for the user to alter the angulation of the tip, thereby reducing the time needed to complete the intubation process. In one advantageous embodiment, the tip is deflectable by mechanical actuation where the user need only pull a lever of the grip handle to deflect the tip. In another advantageous embodiment, the video stylet is provided having a pistol-type grip with a trigger-type lever, thereby facilitating easy gripping and manipulation by the user. It is contemplated that the tip will be deflectable in one plane, however, it is understood that the tip may further be deflectable in multiple planes with the addition of further controls.

The video stylet may also be provided with a camera that is detachably connected to a proximal end of the video stylet. The camera may be provided with image processing circuitry and may receive image data from the imaging device on the distal end of the video stylet. In an alternative embodiment, the video stylet is provided with fiber optical cables running along a longitudinal length of the video stylet such that light from the area ahead of the distal end of the video stylet is picked up and transmitted to the camera, which in turn, processed the received light into image data. In yet another embodiment, a light source, for example, an Light Emitting Diode (LED) is positioned at the distal end of the video stylet (either in the detachable camera or in the video stylet itself), for generating illuminating light. The illuminating light is transmitted through the video stylet via illumination cable (fiber optic cables) to an area ahead of the distal end of the video stylet.

The video stylet may further be provided as either a wired or wireless device. For example, the device may include a power cable for providing electrical power to the electronics and illuminating device, or electrical power may be provided via battery power (such as a rechargeable battery). Still further, it is contemplated that the video stylet may be wirelessly powered via resonant coupling as disclosed in previous U.S. Patent Application Publication No. 2010/0179384 A1. Likewise, the image data generated by the imaging device may be coupled to a control unit or a directly to a display via a cable (e.g., a digital cable connection) or may be wirelessly transmitted to the control unit or directly to the display. It is also contemplated that the control unit may comprise a configurable control unit, such that, upon connection of the video stylet with the control unit, the control unit automatically identifies the particular video stylet and/or associated camera and configures itself to properly function with the video stylet to, for example, process image data from, and receive/send control and/or command signals with the particular video stylet. In this particular embodiment, the video stylet and/or the detachable camera may comprise storage having video stylet and/or camera information identifying the type of video stylet and/or camera. Still further, the storage may comprise video stylet and/or camera use and maintenance data, which may be updated as the video stylet and/or camera are used. Additionally, all of the image data, control/command, maintenance and/or use data may be transmitted and stored over a network connection.

It is contemplated that the video laryngoscope may be provided with similar functionality as discussed in connection with the video stylet except that the laryngoscope imaging device is positioned typically at a distal end of the blade coupled to the laryngoscope handle. The laryngoscope may further be provided with, for example, a Macintosh-type of blade the may detachably connectable with the handle of the laryngoscope. The handle of the laryngoscope may also be provided with a piston-type grip facilitating ease of gripping for the user.

By the provision of both the video laryngoscope and video stylet working on conjunction with each other, the user is able to obtain a full view of both the upper and lower portions (shown simultaneously on a display(s)) of the patient's anatomy during the intubation process, which provides for a safer and quicker intubation process.

For this application the following terms and definitions shall apply:

The term "data" as used herein means any indicia, signals, marks, symbols, domains, symbol sets, representations, and any other physical form or forms representing information, whether permanent or temporary, whether visible, audible, acoustic, electric, magnetic, electromagnetic or otherwise manifested. The term "data" as used to represent predetermined information in one physical form shall be deemed to encompass any and all representations of the same predetermined information in a different physical form or forms.

The term "network" as used herein includes both networks and internetworks of all kinds, including the Internet, and is not limited to any particular network or inter-network.

The terms "first" and "second" are used to distinguish one element, set, data, object or thing from another, and are not used to designate relative position or arrangement in time.

The terms "coupled", "coupled to", "coupled with", "connected", "connected to", and "connected with" as used herein each mean a relationship between or among two or more devices, apparatus, files, programs, media, components, networks, systems, subsystems, and/or means, constituting any one or more of (a) a connection, whether direct or through one or more other devices, apparatus, files, programs, media, components, networks, systems, subsystems, or means, (b) a communications relationship, whether direct or through one or more other devices, apparatus, files, programs, media, components, networks, systems, subsystems, or means, and/or (c) a functional relationship in which the operation of any one or more devices, apparatus, files, programs, media, components, networks, systems, subsystems, or means depends, in whole or in part, on the operation of any one or more others thereof.

The terms "process" and "processing" as used herein each mean an action or a series of actions including, for example, but not limited to: the continuous or non-continuous, synchronous or asynchronous; direction of data; modification of data; formatting and/or conversion of data; tagging or annotation of data; measurement, comparison and/or review of data; and may or may not comprise a program.

In one advantageous embodiment a video intubation system including a video stylet for inserting into an ETT and a video laryngoscope having a laryngoscope imager generating image data is provided, where the video stylet comprises a housing having a distal and a proximal end, the housing comprising a pistol-type grip and an control interface. The video stylet also includes a shaft including a distal and a proximal end, the proximal end of the shaft coupled to the distal end of the housing and the distal end of the shaft comprising a deflectable section, where deflection of the deflectable section is controlled by the control interface. The video stylet further includes an illumination source generating illuminating light for illuminating an area ahead of the distal end the shaft and a video stylet imager positioned in the deflectable section of the shaft, the video stylet imager generating image data of an area ahead of the distal end the shaft. The video stylet still further includes a video stylet camera coupled to the housing, the video stylet camera receiving the image data, and a display coupled to the camera and to the laryngoscope imager, the display receiving both the image data from the video stylet imager and the laryngoscope imager. The video intubation system is provided such that both the image data generated by said video stylet imager and the image data generated by the laryngoscope imager are simultaneously displayed.

Other objects of the invention and its particular features and advantages will become more apparent from consideration of the following drawings and accompanying detailed description.

DETAILED DESCRIPTION OF THE INVENTION

Referring now to the drawings, wherein like reference numerals designate corresponding structure throughout the views.

Figures 1, 2:
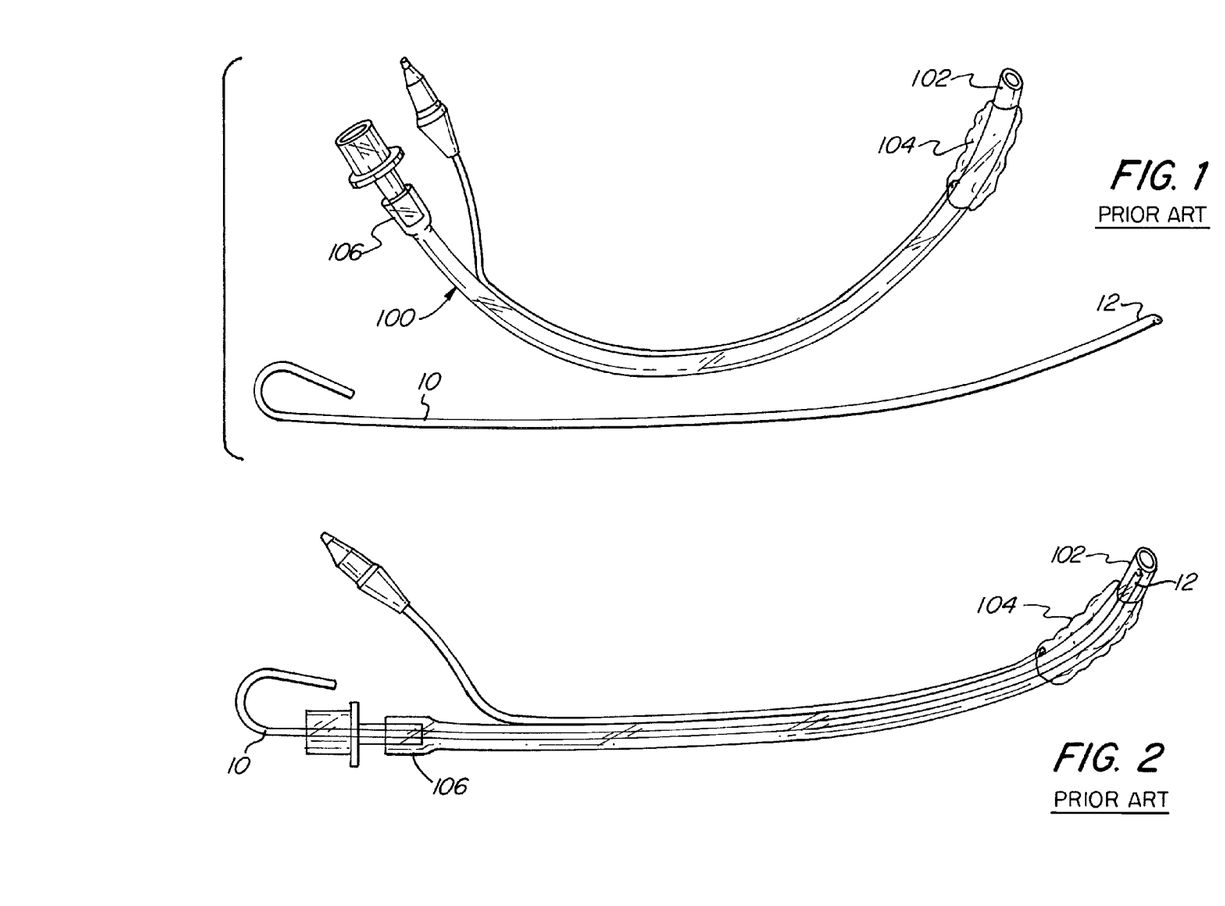
FIG. 1 is an illustration of a stylet and ETT as is known in the prior art.
FIG. 2 is an illustration of the stylet inserted into the ETT according to FIG. 1.

FIGS. 1 and 2 illustrate a stylet 10 and ETT 100, as is known in the prior art. As previously discussed, to intubate a patient, it is known to use a stylet 10, which is typically inserted into the ETT 100 as illustrated in FIG. 2, for introduction into the trachea. Stylet 10 typically comprises a malleable aluminum rod with a plastic cover.

The ETT typically comprises a plastic material with a distal end 102 with an inflatable cuff 104 positioned near distal end 102. Once the ETT has been inserted into the patient's trachea, the inflatable cuff 104 can be expanded to form a seal around the ETT and the inner surface of the trachea. The stylet 10 may be withdrawn and the ETT connected to a machine to facilitate breathing for the patient.

Figure 3:
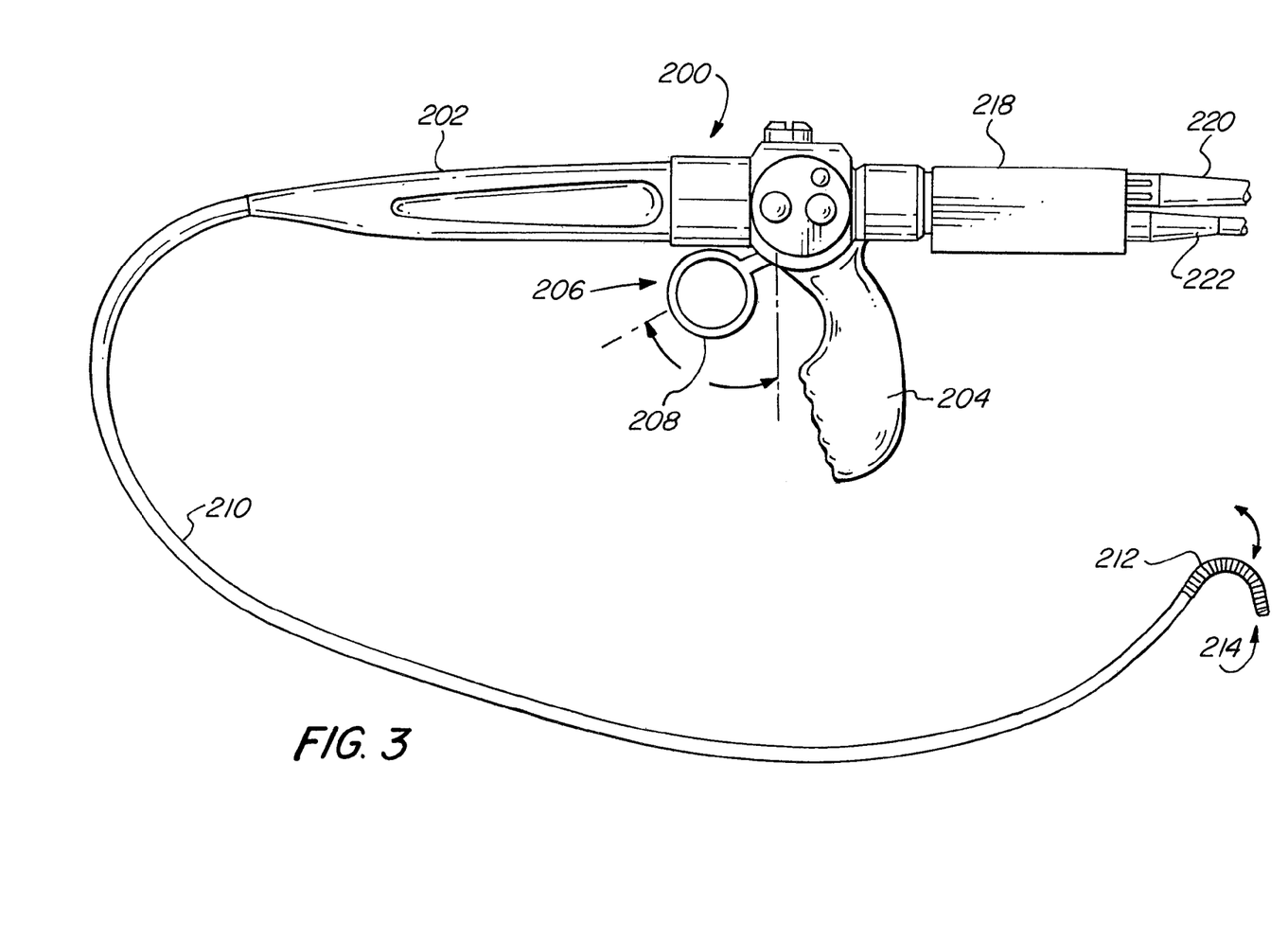
FIG. 3 is an illustration of the video stylet according to one advantageous embodiment of the present invention.

FIG. 3 is an illustration of one advantageous embodiment of the video stylet 200. The video stylet 200 includes a housing 202 having a handle 204, which in this illustration, is provided in the form of a pistol-type grip with a control interface 206. In this particular embodiment, the control interface 206 is provided in the form of a trigger-type lever having a closed loop 208 into which a user may insert a finger.

The video stylet 200 also includes a shaft 210 coupled at one end to the housing 202. Shaft 210 further includes a deflectable section 212 located at a distal end 214 of shaft 210. Actuation of control interface 206 allows a user to actuate deflectable section 212 as indicated by the arrows in FIG. 3.

Figure 4:
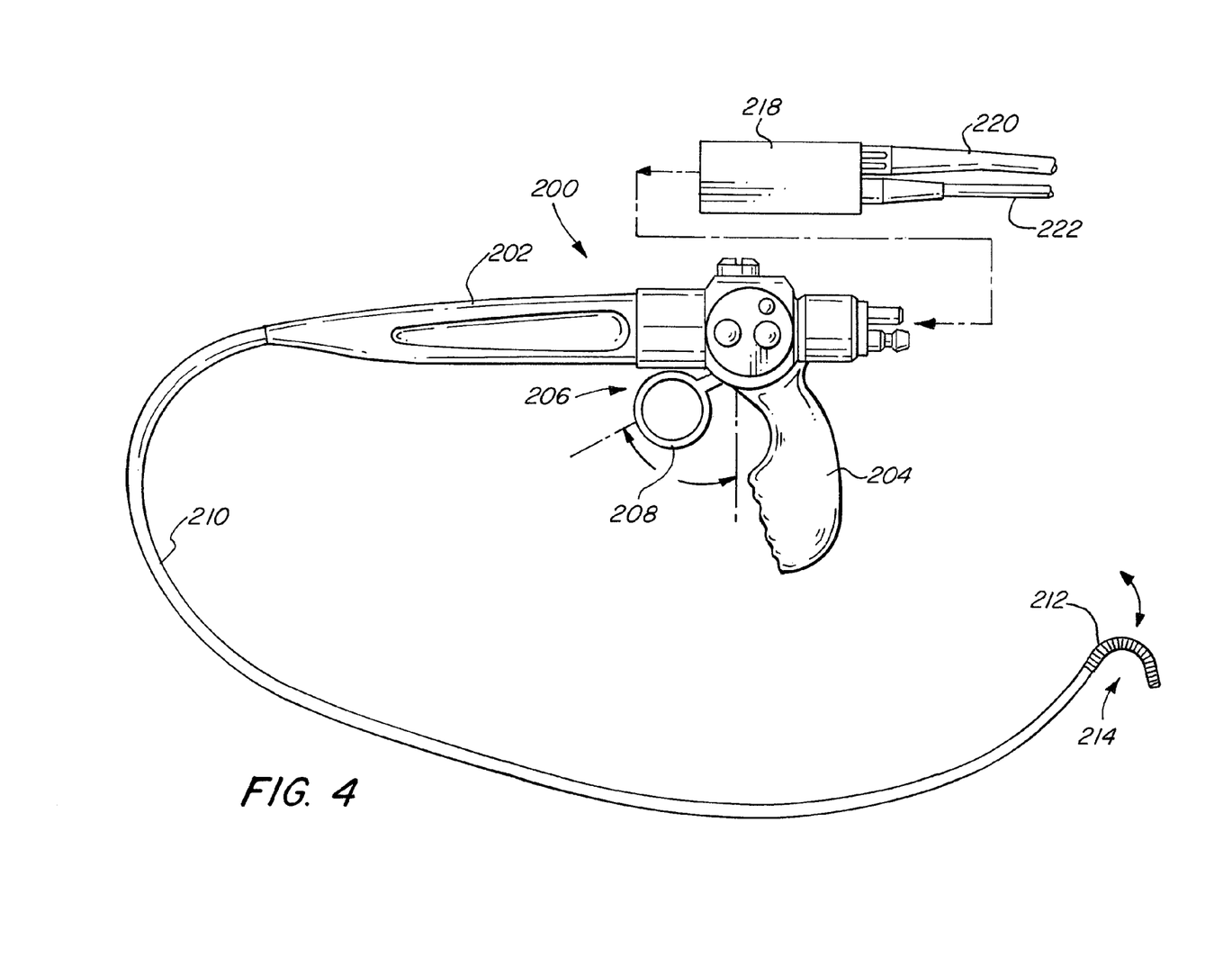
FIG. 4 is an illustration of the video stylet with the camera detached from the video stylet.

Camera 218 may be provided detachably coupled (FIG. 4) to housing 202 such that different cameras (218, 218' . . . 218″) may be attached to housing 202. In the advantageous embodiment illustrated in FIG. 3, camera 218 is provided with multiple channels for transmitting power and information. For example, it is contemplated that illuminating light may be provided via an optical channel 222 (which may comprise fiber optic cables), while image data may be transmitted from camera 218 via data channel 220 (which may comprise two or more copper wires). While optical channel 222 and data channel 220 are illustrated as comprising two different cables, it is understood that both may be consolidating as a single cable surrounded by a protective jacketing (not shown). Illuminating light will then be transmitted from camera 218 through housing 202 and shaft 210 out the distal end 214 to illuminate the area ahead of the shaft. Reflected light is then picked-up and transmitted back to camera 218, which converts the received light to image data. It is contemplated that the transmitted and received light may be transmitted via coherent optical fibers.

Figure 6:
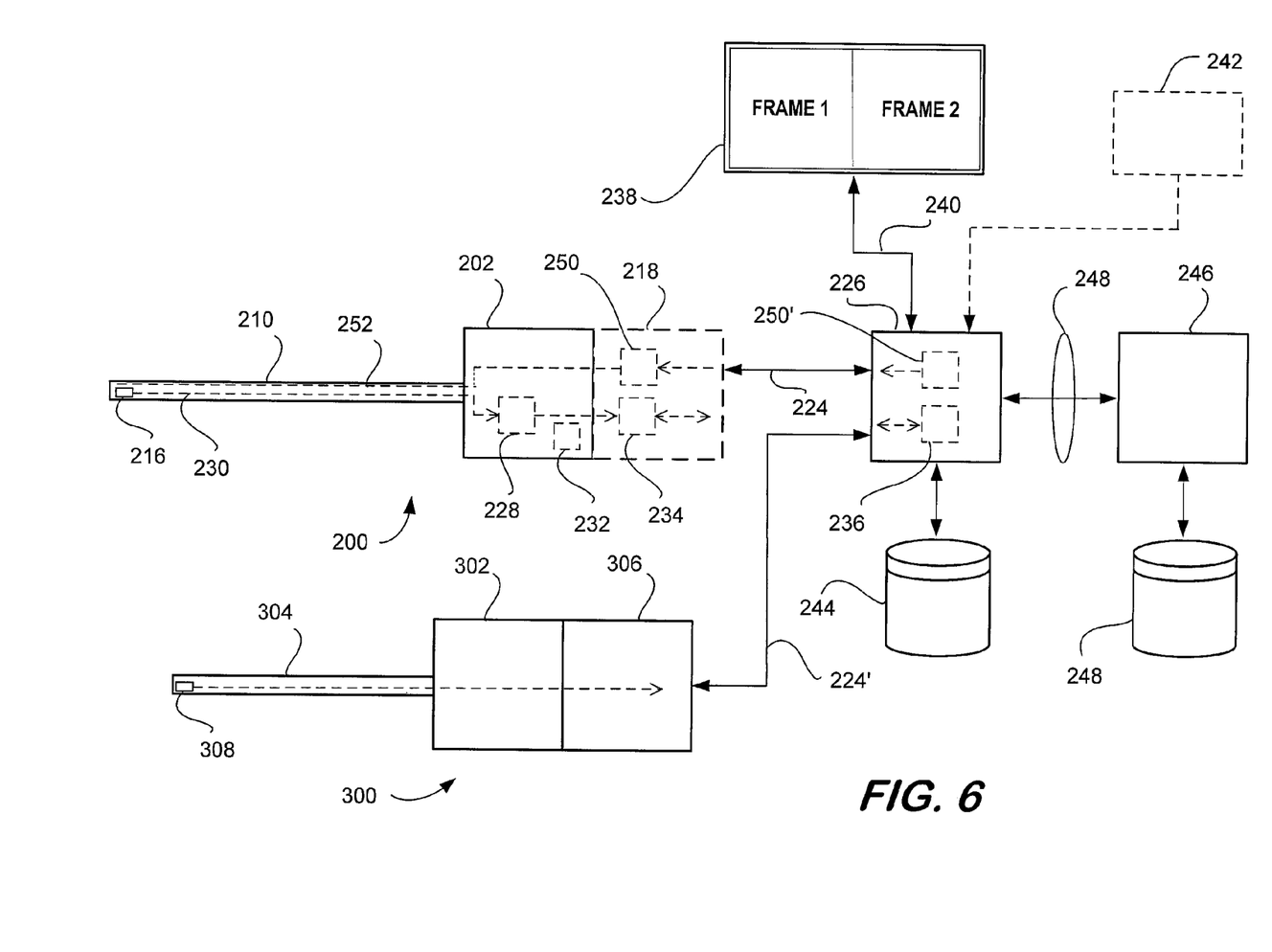
FIG. 6 is a block diagram of the video stylet according to FIG. 3.
Figure 7:
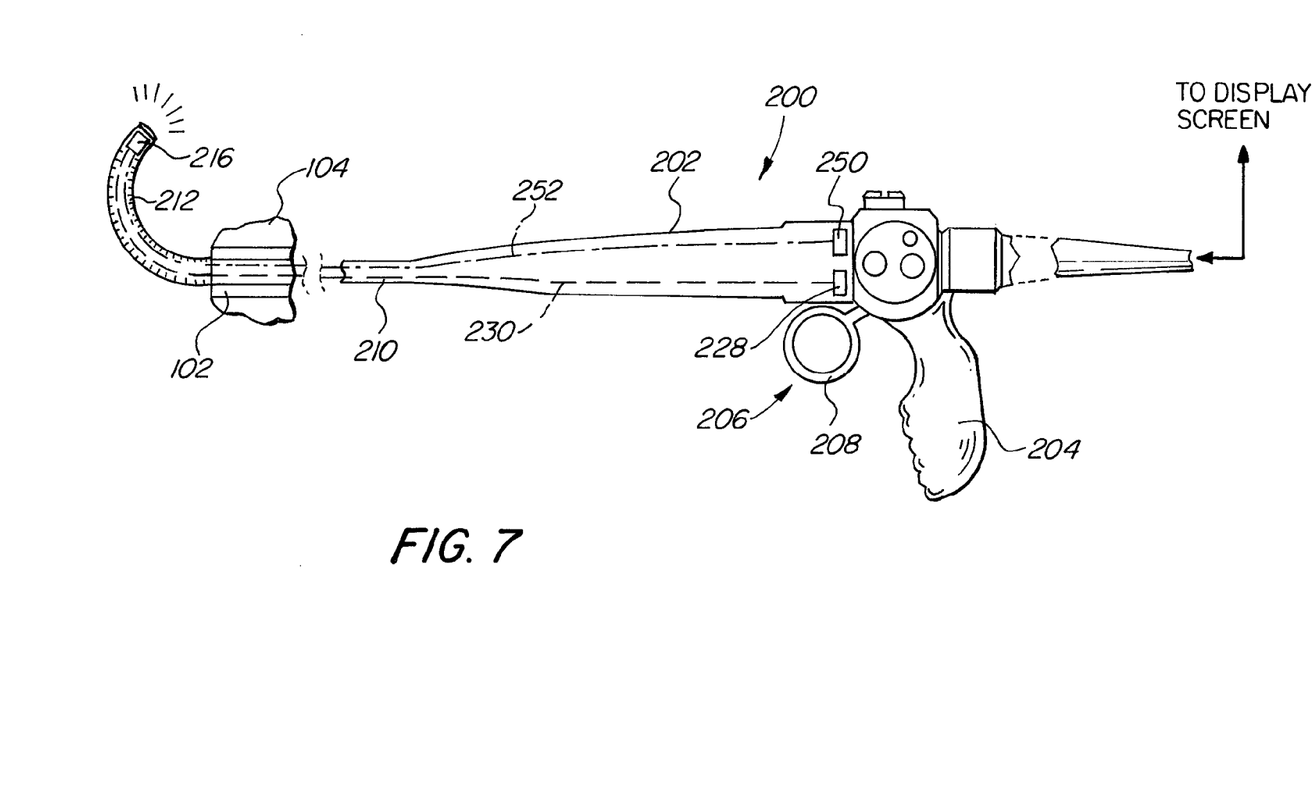
FIG. 7 is an illustration of the video stylet according to FIG. 3.
Figure 8:
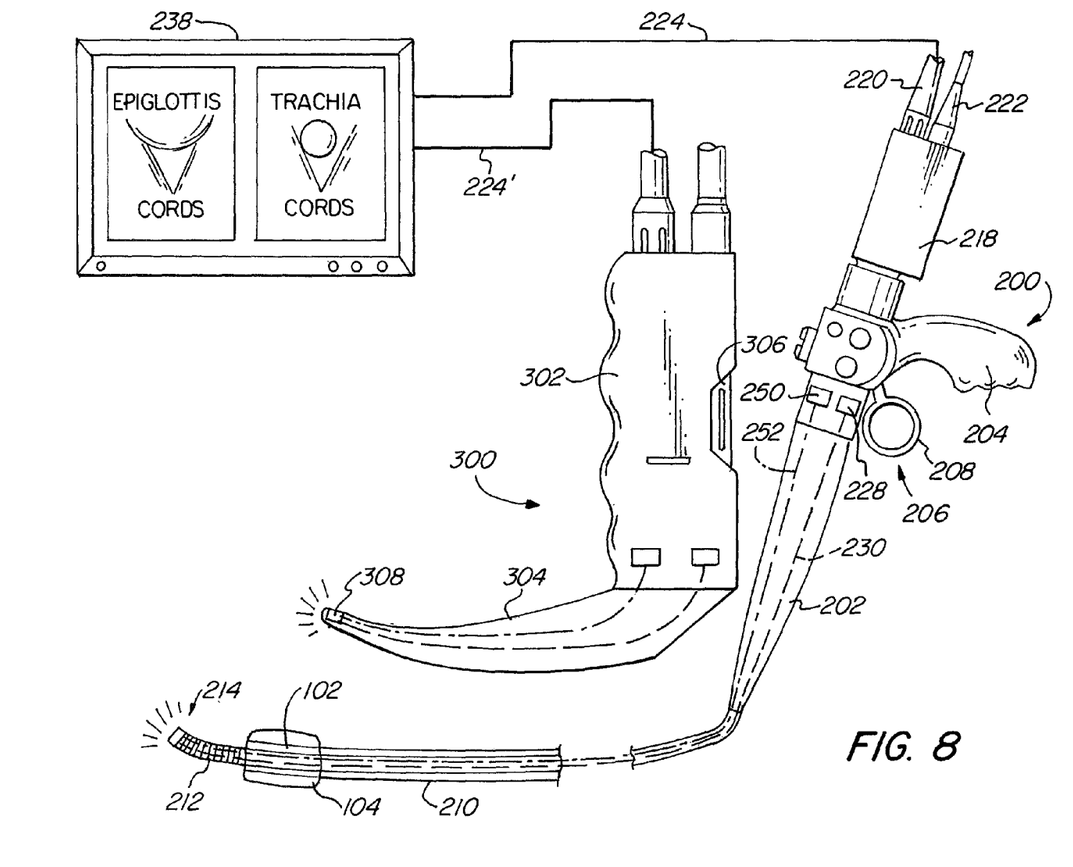
FIG. 8 is an illustration of a video intubation system including the video stylet according to FIG. 3 and a video laryngoscope providing simultaneous images on a display(s).

In an alternative embodiment, a video stylet imager 216 is located at the distal end 214 (see FIG. 7). Video stylet imager 216 is provided to convert received light into digital image data, which in turn, is transmitted to housing 202 on onward to a display (FIGS. 6 & 8). It is contemplated that video stylet imager 216 may comprise virtually any type of digital imaging device, including, but not limited to, a CMOS device or a CCD.

Figure 5:
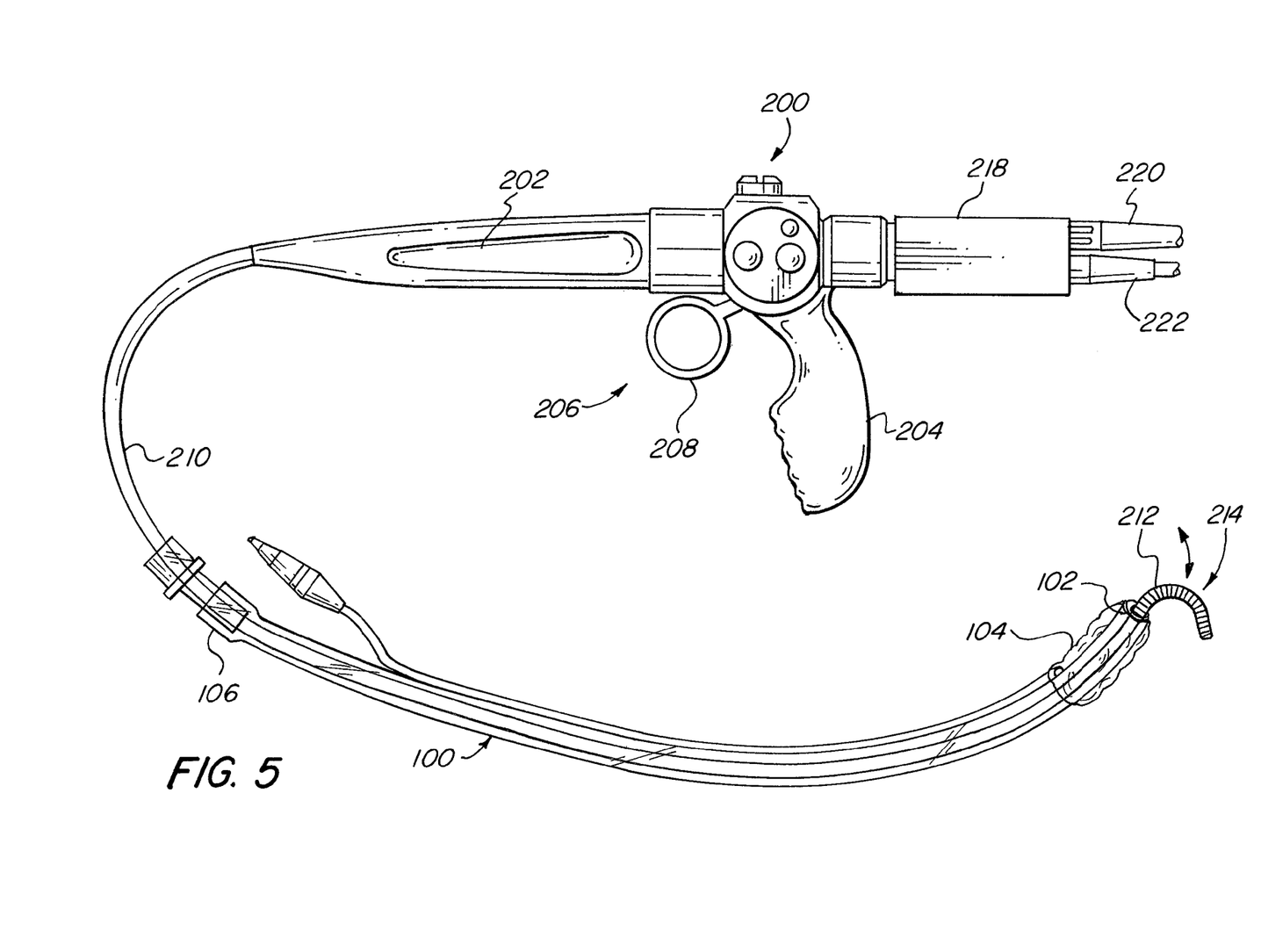
FIG. 5 is an illustration of the video stylet inserted into an ETT according to FIG. 3.

As illustrated in FIG. 5, the video stylet 200 may be used in conjunction with ETT 100. For example, shaft 210 may be inserted into a proximal end 106 of ETT 100. The distal end 102 of ETT 100 may then be guided by a user controlling the movement of deflectable section 212. This provides a distinct advantage over the prior art stylet 10. For example, when a user intubates a patient with stylet 10, the user must pre-bend the stylet 10 (typically made of a malleable alloy) to provide a particular bend radius to distal end 102. However, because of various anatomical anomalies and variations from patient to patient, if the bend radius is not correct to guide the ETT/stylet through the patient's anatomy (e.g., through the vocal cords and into the trachea so that the cuff can then be inflated), the user will be required to remove the ETT/stylet (100,10), adjust the bend of the distal end 12 of stylet 10, and try to intubate the patient a second time. However, with the video stylet 200, the user need only view the image data being transmitted by the video stylet imager 216 and actuate the control interface 206 to adjust the bend radius of distal end 102 to the desired angle for the particular patient without the need to remove ETT 100. This results in a faster intubation with a lower chance of causing damage to the patient during the intubation process.

Figure 9:
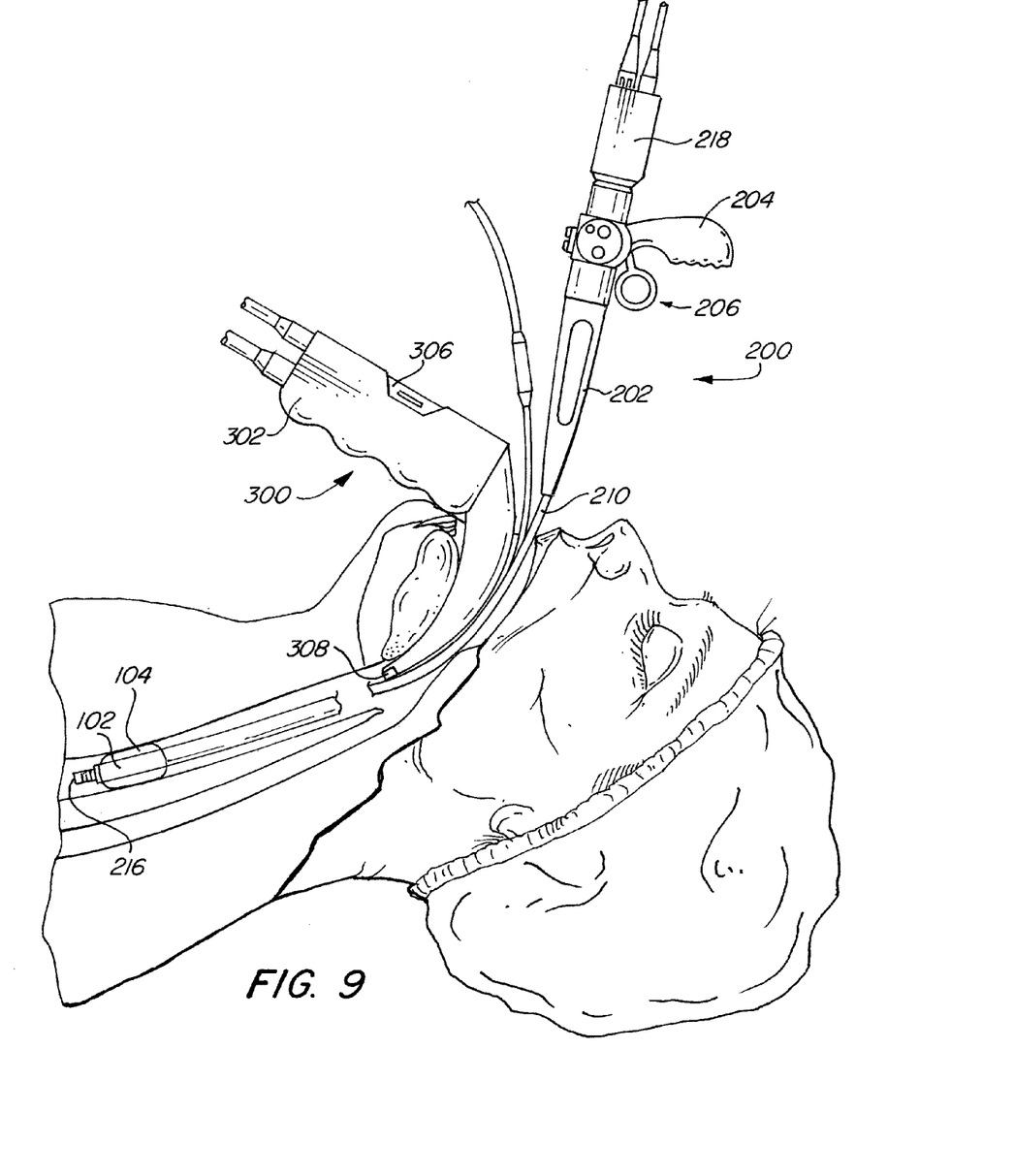
FIG. 9 is an illustration of the video intubation system according to FIG. 6.

Referring now to FIGS. 6-9, FIG. 6 is a block diagram of a video intubation system, and FIGS. 7-9 are illustrations of various embodiments of the video stylet 200 used in conjunction with a video laryngoscope 300. The video intubation system is illustrated in these embodiments comprising the video stylet 200 with (or without) detachable camera 218 coupled to housing 202. The camera 218 is shown (FIGS. 8 & 9) coupled to a control unit 226 via a cable 224 (which may comprise, for example, optical channel 222 and data channel 220); while cable 224' is provided for video laryngoscope 300. Alternatively, it is understood that camera 218 may be wirelessly coupled to control unit 226. Still further, the camera 218 may be replaced by use of a video stylet imager 216, which may be positioned at the distal end 214 of the shaft 210. In this embodiment, image data is generated by the video stylet imager 216 and transmitted to the display.

Inside housing 202 video stylet electronics 228 is illustrated. Video stylet electronics 228 is shown coupled to video stylet imager 216 via an image data channel 230. An arrow is provided to indicate that image data generated by video stylet imager 216, may in this embodiment, be transmitted to video stylet electronics 228. Video stylet electronics 228 may or may not be utilized, and when utilized may comprise, but is not limited to, processing circuitry, amplification circuitry, memory (e.g., cache memory), etc. Also illustrated in housing 202 is storage 232, which is provided as a memory to storage video stylet information, including but not limited to, identification data, configuration data, use data and maintenance data. Storage 232 may further be provided to store image data as needed.

The image data may, in certain embodiments, be transmitted from video stylet electronics 228 to camera electronics 234 (when used), which may be provided to generate image data from the received reflected light. Alternatively, the image data may be generated by the video stylet imager 216 and received by video stylet electronics 228 for transmission to the display. In various advantageous embodiments, the generated/processed image data may be transmitted to control unit 226 via cable 224 (or wirelessly). The control unit may be used to further process the information (by means of control unit electronics 236) and/or transmit the image data to display 238 via connection 240. It should be noted that cable 224 coupling camera 218 to control unit 226 is illustrated with a two-way arrow, which is provided to indicate two-way communication. For example, the video stylet 200 transmits video stylet information, such as, for example, identification/use/maintenance data to control unit 226. Control unit 226 may then use this information to automatically configure to function properly with video stylet 200. Additionally, command and control data may be transmitted to video stylet 200 from control unit 226, and image data is also transmitted from video stylet 200 to control unit 226. It is contemplated that in one embodiment, an input device 242 (keyboard, mouse, track pad, microphone, etc.) may be used by a user to provide input commands for the system. It is further contemplated that rather than having a separate input device 242 (optional), that display 238 may be provided as a touch screen control device, which may be used to display both image data and provide for control/command inputs.

Also shown coupled to control unit 226 is a storage device 244, which is provided to store, for example, the received image data. Storage device 244 may comprise virtually any type of digital storage device and may be internal or external to control unit 226, including a magnetic, high density hard drive, a writable medium including a CD/DVD, or card inserted into the screen casing including, for example, a removable drive, such as a thumb drive, volatile or non-volatile memory, etc. It is further contemplated that storage 244 may have saved thereon, configuration data for configuration of control unit 226 so that control unit 226 may properly process the received image data and control video stylet 200.

Control unit 226 is further shown coupled to computer 246 via a network connection 248. It is contemplated that network connection 248 may comprise, for example, an Internet connection. Computer 246 is further coupled to a remote storage 248, which may comprise virtually any type of memory device as is described in connection with storage 244. Additionally, virtually any type of digital data may be saved on remote storage 248, such as, but not limited to, configuration data, update information, image data, etc.

An illumination source 250 is also shown in camera 218. It should be noted that illumination source 250 may be positioned in camera 218 (as illustrated), or in housing 202 or be positioned in control unit 226 (indicated as illumination source 250'). In the case where illumination source 250 is positioned in either camera 218 or housing 202, cable 224 would then only comprise a digital transmission cable for transmitting image data, control/command data, update, use, maintenance data, etc. However, in the embodiment where the illumination source 250' is positioned in control unit 226, cable 224 would then be provided with a fiber optic channel for transmission of illuminating light from illumination source 250' to video stylet 200. In either case, illuminating light is transmitted via illuminating light channel 252.

Also illustrated in FIGS. 6, 8 and 9 is video laryngoscope 300, which is provided with a housing 302, a blade 304 coupled to housing 302 and a camera 306 (if necessary) coupled to housing 302. The blade 304 may be provided with a laryngoscope imager 308, which may comprise, for example, a CCD and/or CMOS device. Laryngoscope imager 308 may, in one advantageous embodiment, be positioned on an underside of blade 304 and generates image data, which is transmitted to camera 306. Alternatively, a camera 306 may be used to generate the image data. If camera 306 is used, it may then be coupled to control unit 226, otherwise, the image data generated by the laryngoscope imager 308 may be transmitted to control unit 226. It is contemplated that control unit 226 may identify laryngoscope 300 upon connection and automatically configure itself based on the identification. Once configured, control unit is able to properly process the received image data from laryngoscope 300. It should be noted that, like video stylet 200, the connection between video laryngoscope 300 and control unit 226 may be either wired or wireless. Additionally, it is understood that control unit 226 need not be used, rather, the image data may be transmitted directly to the display.

The video laryngoscope 300 has similar functionality as video stylet 200, and therefore the various functions and features of video laryngoscope 300 will not be reiterated.

In yet another advantageous embodiment, display 238 is provided comprising a single display having a split frame (Frame 1 and Frame 2; FIGS. 6 and 8). It is contemplated that control unit receives first image data from video stylet 200 and second image data from video laryngoscope 300. These two video streams may be combined into one digital video stream (e.g., may be multiplexed) that is transmitted to display 238 and presented as a split-screen display (e.g., simultaneous presentation of video stylet image data stream in Frame 1 and video laryngoscope image data stream in Frame 2). While a single display 238 is illustrated, it is contemplated that multiple displays could be utilized positioned, for example, side-by-side.

FIG. 9 is an illustration of both video stylet 200 and video laryngoscope 200 each generating and transmitting image data. It should be understood that the video intubating laryngoscope is used to elevate the tongue and displays the majority of the view of the epiglottis and upper part of the vocal cords. The video stylet, which is introduced below the tongue and the tip directed from the pistol grip simultaneously with the video laryngoscope, displays the lower part of the larynx and clearly shows the introduction into the trachea and displays the proper position of the ETT in relation to the bifurcation (not seen by the blind introduction of the ETT with a standard stylet). Both images can be simultaneously observed, for example, on the split screen.

Although the invention has been described with reference to a particular arrangement of parts, features and the like, these are not intended to exhaust all possible arrangements or features, and indeed many other modifications and variations will be ascertainable to those of skill in the art.

What is claimed is:

1. A video intubation system comprising:
   a video laryngoscope having a video laryngoscope imager generating laryngoscope image data;
   a video stylet having:
   a housing having a distal and a proximal end, said housing comprising a control interface;
   a shaft including a distal and a proximal end, the proximal end of the shaft coupled to the distal end of said housing and the distal end of said shaft comprising a deflectable section;
   wherein deflection of the deflectable section is controlled by the control interface;
   an illumination source generating illuminating light for illuminating an area ahead of the distal end said shaft;
   a video stylet imager generating video stylet image data of an area ahead of the distal end said shaft;
   a video stylet storage having use or maintenance data for said video stylet saved thereon;
   a control unit detachably coupled to said video laryngoscope via a first cable and said video stylet via a second cable, said control unit receiving the laryngoscope image data and the video stylet image data via the first and second cables respectively;
   wherein said illumination source is positioned in said control unit and illuminating light is transmitted to said video stylet via the cable connection;
   a display detachably coupled to said control unit; and
   wherein said control unit processes the laryngoscope image data and the video stylet image data such that the laryngoscope image data and the video stylet image data are received by and presented on a display
   wherein said control unit comprises a control unit storage, separate from the video stylet storage, provided to store the received video stylet image data, wherein said control unit storage comprises configuration data for configuration of said control unit.

2. The video intubation system according to claim 1 wherein said video stylet imager is positioned in the deflectable section of said shaft.

3. The video intubation system according to claim 1 wherein said video stylet imager is positioned in a video stylet camera detachably coupled to said housing.

4. The video intubation system according to claim 1 wherein said video stylet imager is selected from the group consisting of: a CMOS device, a CCD and combinations thereof.

5. The video intubation system according to claim 1 wherein said illumination source comprises an LED.

6. The video intubation system according to claim 1 wherein said control unit comprises a configurable control unit, such that, upon connection of the video stylet with the control unit, the control unit automatically identifies the particular video stylet and is configured based on an identification.

7. The video intubation system according to claim 6 wherein upon connection of the video laryngoscope with the control unit, the control unit automatically identifies the particular video laryngoscope and is configured based on the identification.

* * * * *

UNITED STATES PATENT AND TRADEMARK OFFICE
CERTIFICATE OF CORRECTION

| | | |
|---|---|---|
| PATENT NO. | : 8,652,033 B2 | Page 1 of 1 |
| APPLICATION NO. | : 12/889095 | |
| DATED | : February 18, 2014 | |
| INVENTOR(S) | : Berci et al. | |

It is certified that error appears in the above-identified patent and that said Letters Patent is hereby corrected as shown below:

On the Title page, Item (75) Inventors, insert --Carin A. Hagberg, Bellaire, TX (US)--.

Signed and Sealed this
Twenty-fifth Day of August, 2015

Michelle K. Lee
*Director of the United States Patent and Trademark Office*